United States Patent
Agrawal et al.

(10) Patent No.: US 12,325,682 B2
(45) Date of Patent: Jun. 10, 2025

(54) SYSTEMS AND PROCESSES FOR TURBOQUENCHING

(71) Applicant: PURDUE RESEARCH FOUNDATION, West Lafayette, IN (US)

(72) Inventors: Rakesh Agrawal, West Lafayette, IN (US); Edwin Andres Rodriguez Gil, West Lafayette, IN (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 0 days.

(21) Appl. No.: 18/327,589

(22) Filed: Jun. 1, 2023

(65) Prior Publication Data

US 2023/0391687 A1 Dec. 7, 2023

Related U.S. Application Data

(60) Provisional application No. 63/347,759, filed on Jun. 1, 2022.

(51) Int. Cl.
C07C 4/04 (2006.01)
C07C 2/80 (2006.01)
C07C 5/327 (2006.01)

(52) U.S. Cl.
CPC ............. *C07C 4/04* (2013.01); *C07C 2/80* (2013.01); *C07C 5/327* (2013.01)

(58) Field of Classification Search
CPC .. C07C 4/04; C07C 2/80; C07C 5/327; C07C 7/00; B01D 3/00; B01J 3/00
See application file for complete search history.

(56) References Cited

U.S. PATENT DOCUMENTS

| | | | |
|---|---|---|---|
| 2007/0006566 A1* | 1/2007 | Dean ................. | F02C 3/30 60/39.12 |
| 2010/0130803 A1* | 5/2010 | Keusenkothen ......... | C07C 5/09 422/187 |
| 2014/0378728 A1* | 12/2014 | Davis ................. | C07C 5/325 585/634 |
| 2020/0290939 A1* | 9/2020 | Van Willigenburg ... | C10G 9/36 |
| 2021/0179516 A1* | 6/2021 | Van Willigenburg .... | C07C 4/04 |
| 2023/0135324 A1* | 5/2023 | Oud ................. | C10G 9/36 60/645 |

* cited by examiner

*Primary Examiner* — Ali Z Fadhel
(74) *Attorney, Agent, or Firm* — Edmonds & Cmaidalka, P.C.

(57) ABSTRACT

Systems and processes for quenching a high-temperature, above atmospheric pressure feed to a lower temperature without the need of any quenching fluid and with the additional benefit of coproducing electric power. The systems and processes provided here result in a simpler quenching process, which is particularly beneficial for quenching streams after high-temperature chemical reactions.

20 Claims, 9 Drawing Sheets

SYSTEMS AND PROCESSES FOR TURBOQUENCHING

CROSS-REFERENCE TO RELATED APPLICATIONS

This application claims priority to U.S. Provisional patent application having Ser. No. 63/347,759, filed on Jun. 1, 2022. The entirety of which is incorporated by reference herein.

GOVERNMENT LICENSE RIGHTS

This invention was made with government support under Cooperative Agreement No. EEC-1647722 awarded by the National Science Foundation. The government has certain rights in the invention.

BACKGROUND OF THE INVENTION

Field of the Invention

The embodiments provided herein relate to systems and processes for quenching matter streams. More particularly, the embodiments described herein relate to systems and processes for quenching chemical mixtures or their individual components.

Description of the Related Prior Art

Many chemical processes require a fast reduction in temperature after a high-temperature chemical reaction; otherwise, undesired side reactions or product degradation might take place. The process of rapidly reducing the temperature is often referred to as quenching.

Figure 1:
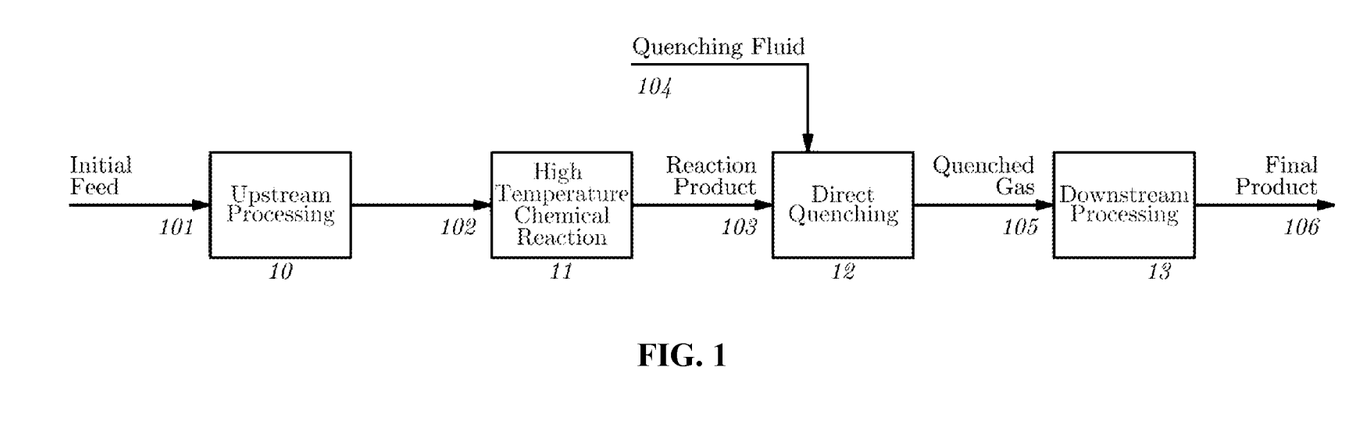
FIG. 1 depicts a block diagram illustrating a general chemical process in which direct quenching is used to lower the temperature of a matter stream after a high-temperature chemical reaction, according to one or more embodiments provided herein.
Figure 2:
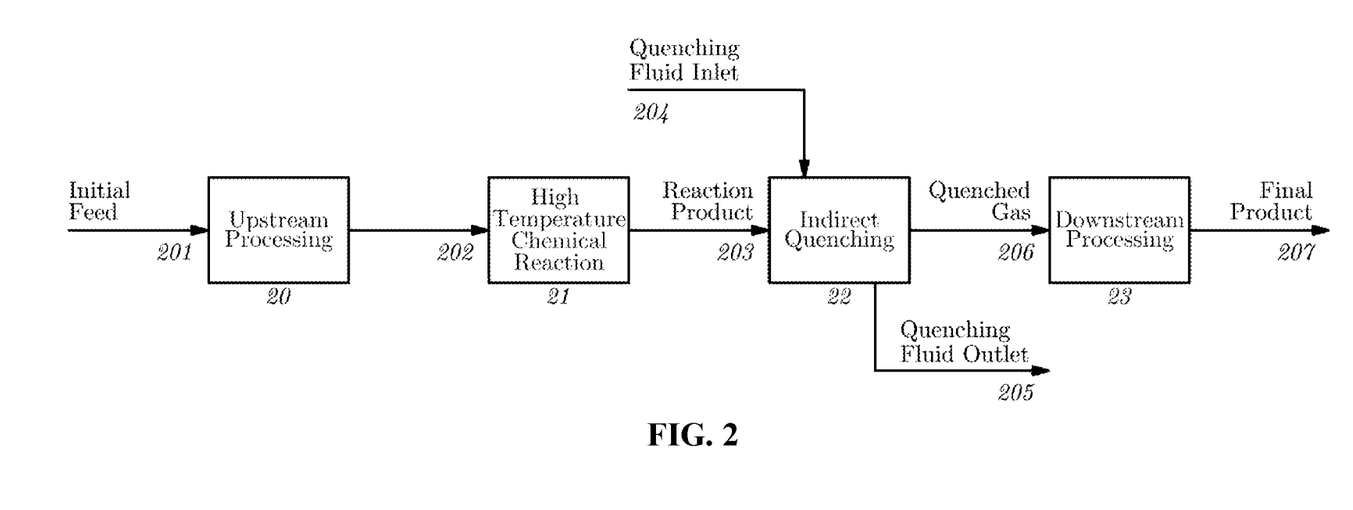
FIG. 2 depicts a block diagram illustrating a general chemical process in which indirect quenching is used to lower the temperature of a matter stream after a high-temperature chemical reaction, according to one or more embodiments provided herein.

Two types of quenching are identified depending on the way the temperature is reduced: direct quenching and indirect quenching. FIG. 1 and FIG. 2 show a schematic representation of the two types of quenching, respectively.

The block diagram in FIG. 1 illustrates a general chemical process in which direct quenching is used to lower the temperature of a stream after a high-temperature chemical reaction. The initial feed, stream 101, is first preprocessed in the upstream processing section, 10. The resulting mixture, stream 102, is then conducted to the high-temperature chemical reaction block, 11, where the stream experiences a change in its chemical composition. The reaction product, stream 103, is then quenched through direct mixing with a quenching fluid, stream 104, in the direct quenching block, 12. The quenching fluid is often a liquid stream such as water or other fluid or combination of fluids. The quenched gas, stream 105, is then conducted to downstream processing, 13. The final product leaves the system as stream 106.

FIG. 2 depicts a block diagram illustrating a general chemical process in which indirect quenching is used to lower the temperature of a stream after a high-temperature chemical reaction. The initial feed, stream 201, is first preprocessed in the upstream processing section, 20. The resulting mixture, stream 202, is then conducted to the high-temperature chemical reaction block, 21, where the stream experiences a change in its chemical composition. The reaction product, stream 203, is then quenched indirectly by the incoming quenching fluid, stream 204, in the indirect quenching block, 22. The quenching fluid absorbs thermal energy from the reaction product through a heat exchanger and then leaves the process as stream 205. Unlike in direct quenching, there is no direct contact between the quenching fluid and the reaction product. In this way, only the heat energy is transferred. The quenched gas, stream 206, is then conducted to downstream processing, 23. The final product leaves the system as stream 207.

Indirect quenching is not as fast as the corresponding direct quenching. Furthermore, indirect quenching requires large temperature differences across the heat exchangers to increase heat transfer rates, thereby severely degrading the quality of the heat recovered from the reaction product since this heat is collected by the quenching fluid at a much lower temperature. Indirect quenching often requires special designs of heat exchangers to enhance heat transfer, thus making them costly.

Figure 3:
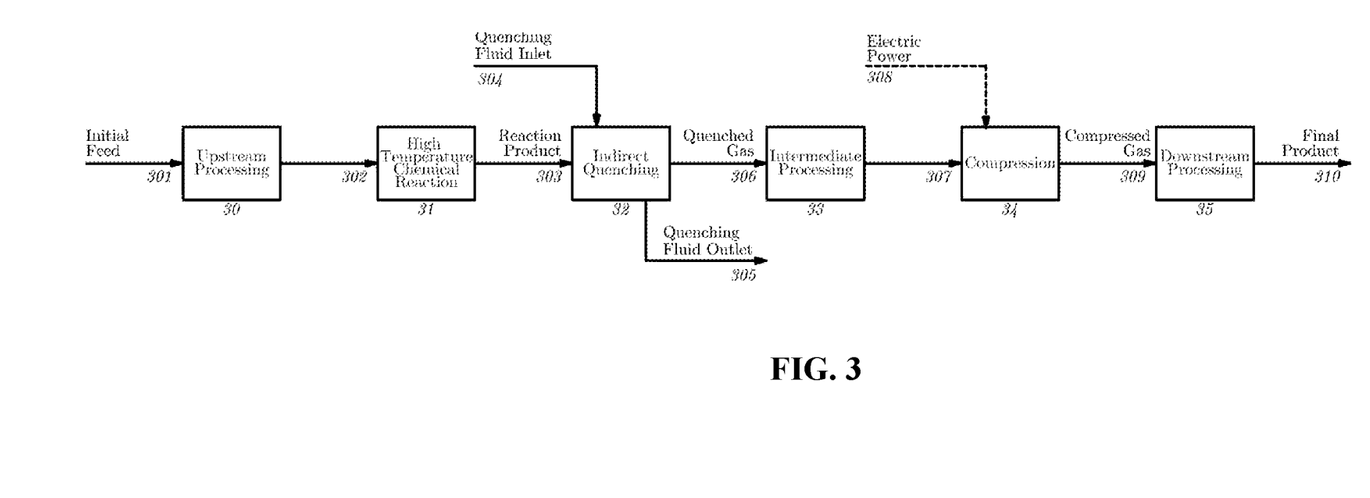
FIG. 3 depicts a block diagram illustrating a general process in which a matter stream is compressed after an intermediate processing step, which in turn is preceded by indirect quenching. The compression step uses electric power for operation and is succeeded by a downstream processing step, according to one or more embodiments provided herein.

In certain cases, a compression step takes place at some point after quenching. This situation is illustrated in FIG. 3, where the quenched gas, stream 306, is conducted to an optional intermediate processing section, 33, to later enter the compression block, 34, which requires electric power, 308, for operation. The compressed gas, stream 309, is then directed to downstream processing, 35, and finally leaves the system as the final product stream, 310. Although FIG. 3 uses indirect quenching as an example, the process would be analogous in case of using direct quenching.

Quenching is used in the production of many chemical products, for instance, in the production of ethylene through the steam cracking process, hydrogen through steam methane reforming, and syngas through partial oxidation of methane.

Figure 4A:
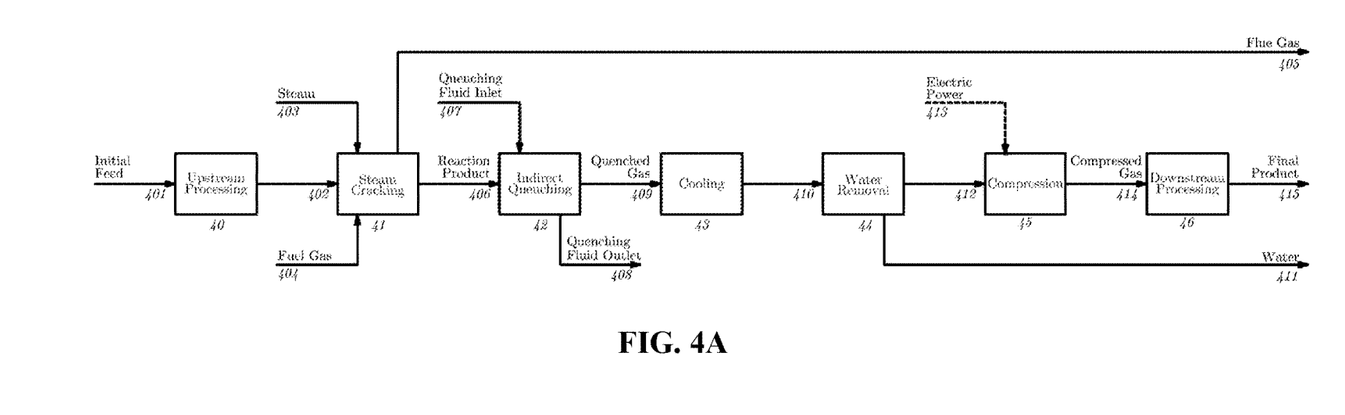
FIG. 4A depicts a block diagram illustrating a general process in which a matter stream is compressed as an example of a quenching application, according to one or more embodiments provided herein.
Figure 4B:
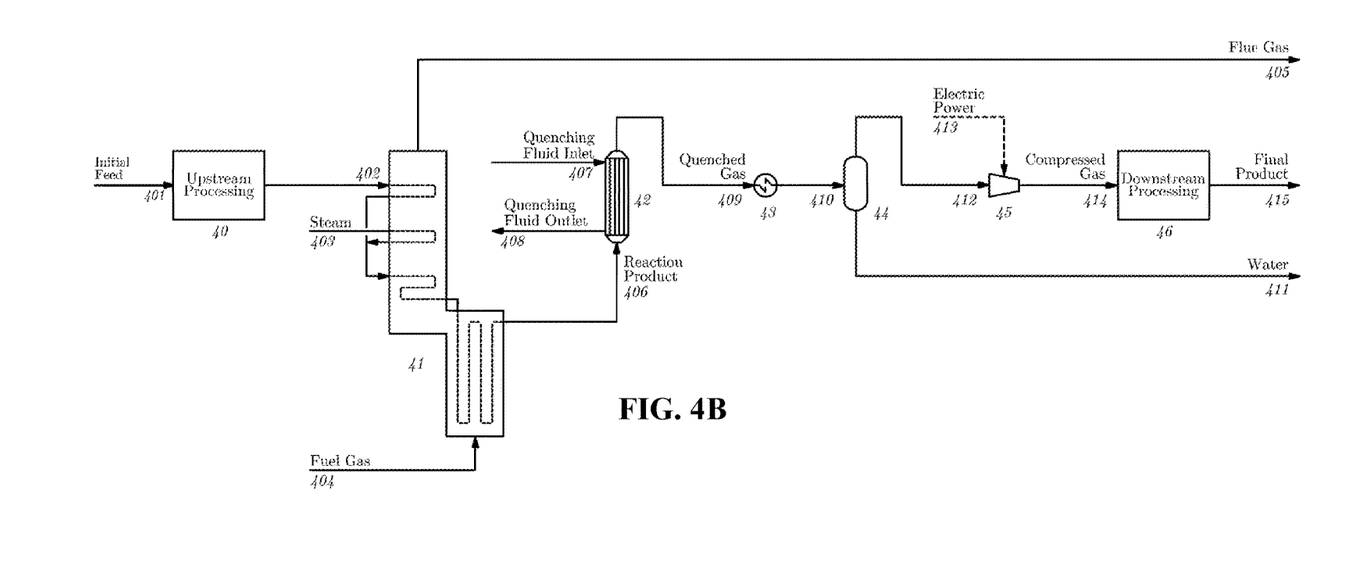
FIG. 4B shows additional detail of the general cracking process illustrated in FIG. 4A, according to one or more embodiments provided herein.

FIGS. 4A and 4B illustrate a general process in which a matter stream is compressed as an example of the application of quenching. The initial feed, stream 401, is first conducted to upstream processing, 40. In practice, this block might include many unit operations including, for example, acid gas removal, cryogenic distillation, and/or dehydration. The resulting stream, 402, is then conducted to the cracking reactor, unit 41, where it can react in the presence of steam, stream 403, to form the reaction product, stream 406. This reaction is endothermic, which means that it can require an external supply of energy to react. In this case, the energy is provided by the combustion of the fuel gas, stream 404, inside the cracking furnace. The combustion gases can be used to preheat the reaction feed and then can leave the system as flue gas, stream 405. The reaction product must be rapidly cooled (quenched); otherwise, significant levels of product degradation take place, in addition to unwanted side reactions. For ethylene production, indirect quenching can be the main quenching technology used in practice, but direct quenching can also be used. The reaction product, stream 406, is conducted to block 42, where the quenching fluid, stream 407, indirectly absorbs thermal energy from it to lower its temperature. For this process, the quenching fluid can be water or another fluid or a combination of fluids, which can vaporize inside the heat exchanger, 42, to then leave in the quenching fluid outlet, stream 408. The quenched gas, stream 409, is then conducted to a secondary cooling unit, 43, and later to water removal, 44, which could be considered as intermediate processing using the notation in FIG. 3. The resulting stream, 412, is then conducted to compression, unit 45, which can use electric power, 413, for operation. FIG. 4B shows only one compressor as a simplification. However, in practice, a series of multiple compressors and intermediate cooling stages can be used, depending on the level of compression required. The compressed gas, stream 414, is then conducted to downstream processing, unit 46, to finally leave the system as the final product stream, 415. Besides the substantial degradation of heat across the heat exchanger 42, an additional drawback of this system is that a fluid purification unit is needed to supply water in adequate conditions for quenching, which adds cost and operational complexity to the process. Furthermore, the use of the steam generated during quenching, 408, must be found to keep the process efficient. Condensing steam turbines may be used to extract power from the resulting steam, with the drawback of further adding cost to the process.

Despite the specific type, quenching is an expensive unit operation. It requires high capital cost, large amounts of quenching fluid, and specialized control systems. Consequently, its implementation is limited to large-size applications. There is still a need, therefore, for a simpler and more efficient way to quench.

SUMMARY OF THE INVENTION

Systems and processes for turboquenching are provided. The systems and processes do not require quenching fluid and can coproduce electric power. As such, systems and processes provided herein provide a simpler, cheaper, and smaller alternative for quenching.

In at least one embodiment, the process can include one or many turboquenching units connected in series or parallel. In at least one embodiment, the turboquencher can provide electrical power to other sections of the plant through an electric generator. In at least one embodiment, the turboquencher can provide electric power for compression through coupling with an electric motor. In at least one embodiment, the turboquencher is mechanically coupled with the compression section to reduce the number of process units. In at least one embodiment, the compression sections can include one or multiple compressors connected in series or parallel with the presence or absence of intermediate processes.

In at least one other embodiment, processes for quenching a high-temperature and above atmospheric pressure stream to a lower temperature without the need of a quenching fluid is provided. The process can include providing an outlet stream from a high temperature conversion reaction, wherein the outlet stream has a temperature of 500° C. or above and a pressure above atmospheric pressure; expanding the outlet stream to generate work and provide a quenched stream; and recovering the work.

In another embodiment, the process can include providing an outlet stream from a high temperature conversion reaction, wherein the outlet stream has a temperature of 500° C. or above and a pressure above atmospheric pressure; expanding the outlet stream to provide work and a quenched stream; recovering the work to provide electrical power; and compressing the quenched stream using the electrical power.

In at least one other embodiment, processes for upgrading natural gas liquids (NGL) are also provided. Such process can include providing a natural gas comprising methane and one or more $C_{2+}$ hydrocarbons; dehydrogenating at least a portion of the one or more $C_{2+}$ hydrocarbons to provide an outlet stream comprising one or more $C_{2+}$ olefinic hydrocarbons at a temperature of 550° C. to 950° C. and a pressure above atmospheric pressure; expanding the outlet stream to generate work and provide a quenched stream comprising the one or more $C_{2+}$ olefinic hydrocarbons at a temperature lower than the inlet temperature; recovering the work to provide electrical power; compressing the quenched stream using the electrical power; and oligomerizing the compressed stream to provide a product stream comprising one or more C4 to C26 oligomers.

BRIEF DESCRIPTION OF THE DRAWINGS

To explain the manner in which the above-recited features of the present invention is understood in detail, a more particular description of the invention, briefly summarized above, is given in reference to the embodiments, some of which are illustrated in the appended drawings. It can be noted, however, that the appended drawings illustrate only typical embodiments of this invention and are therefore not to be considered limiting of its scope, for the invention may admit to other equally effective embodiments.

The accompanying drawings are incorporated into and form a part of the specification to illustrate aspects and examples of the present disclosure. These figures, together with the description, serve to explain the general principles of the disclosure. The figures are only for the purpose of illustrating examples of how the various aspects of the disclosure is made and used and are not to be construed as limiting the disclosure to only the illustrated and described examples. It is further emphasized that the figures are not necessarily to scale; certain features and certain views of the figures are shown as exaggerated in scale or in schematic for clarity and/or conciseness.

DETAILED DESCRIPTION

Certain terms are used throughout the following description and claims for the purpose of referring to particular components. As someone skilled in the art will appreciate, various entities can refer to the same component using different names, and as such, the naming convention for the elements described here is not intended to limit the scope of the invention, unless otherwise specifically defined here. Further, the naming convention used here is not intended to distinguish among components that differ in name but not function. Furthermore, in the following discussion and in the claims, the terms "including" and "comprising" are used in an open-ended fashion, and thus should be interpreted to mean "including, but not limited to."

The indefinite articles "a" and "an" refer to both singular forms (i.e., "one") and plural referents (i.e., one or more) unless the context clearly dictates otherwise.

The term "or" is intended to encompass both exclusive and inclusive cases: i.e., "A or B" is intended to be synonymous with "at least one of A and B" unless otherwise expressly specified here.

The term "cooling" refers to the reduction in temperature.

The term "quenching" refers to the fast cooling a matter stream.

The term "turboquenching" refers to a quenching process in which the pressure of the quenched stream is dropped from high pressure to a lower pressure while generating work. Generally, this can be done by expansion in a turboexpander while recovering work.

The term "quenched steam" refers to a matter stream that has been subjected to quenching.

The term "quenched gas" refers to a quenched stream which is in gas state at the process conditions.

The term "quenching fluid" refers to a fluid or combination or fluids used for quenching of the quenched stream.

The term "direct quenching" refers to a quenching process in which there is direct contact between the quenching fluid and the matter stream subjected to quenching.

The term "indirect quenching" refers to a quenching process in which there is no direct contact between the quenching fluid and the matter stream subjected to quenching. The term "chemical process" refers to a process in which there is a change in the chemical composition of one or more matter streams.

The term "high-temperature chemical reaction" refers to a chemical process that takes place above the ambient temperature.

The terms "undesired reactions" or "unwanted reactions" are used interchangeably and refer to chemical processes that lead to undesired changes in the chemical composition of one or more matter streams.

The term "endothermic reaction" refers to chemical process that require external energy input to take place.

The term "product degradation" refers to a process by which the desired product undergoes undesired reactions.

The term "compression" refers to the increase in pressure of one or more matter streams.

The term "compressed gas" refers to a gas stream whose pressure is above ambient pressure.

The term "expansion" refers to a gain or increase in volume due to a reduction in pressure of one or more matter streams.

The term "generator" refers to a device that transforms mechanical work into electric power.

The terms "higher temperature process" and "higher temperature processing" are used interchangeably and refer to a process that takes place above the ambient temperature.

The terms "upstream processes" and "upstream processing" are used interchangeably and refer to any processing steps and/or unit operations that take place before a high-temperature chemical reaction.

The terms "intermediate processes" and "intermediate processing" are used interchangeably and refer to any processing step and/or unit operation that takes place between quenching and compression.

The terms "downstream processes" and "downstream processing" are used interchangeably and refer to any processing step and/or unit operation that takes place after quenching, in the case where compression is not present, and after compression in the case where is present.

The term "hydrocarbon" refers to chemical compounds made mostly of hydrogen and carbon atoms.

The term "paraffin(s)" refers to a mixture of one or more saturated hydrocarbons.

The term "olefin(s)" refers to a mixture of one or more unsaturated hydrocarbons.

The terms "natural gas liquids" or "NGLs" are used interchangeably and refer to a mixture of hydrocarbons that includes ethane, propane, butane, isobutane, and natural gasoline.

The terms "initial feed" or "gas feed" are used interchangeably and both refer to any gaseous mixture that naturally contains methane and one or more other hydrocarbons. Illustrative gas mixtures are or can include a raw shale gas stream or raw natural gas stream or other raw hydrocarbon stream that is obtained directly (i.e. without processing to remove water and/or acid gas) from a reservoir, wellhead, or pipeline. Suitable gas mixtures can also originate from a refinery, such as from a FCC, coker, steam cracker, and pyrolysis gasoline (pygas). Suitable gas mixtures can also be or can include coal gas. Illustrative gas mixtures can also be or can also include a gas that has been treated for acid gas and water removal. For simplicity and ease of description, the detailed description provided herein makes specific references to "shale gas" or "natural gas" or "dry shale gas" or "sweet and dry shale gas"; however, those same references equally apply to any gas mixture containing at least 50 mol % methane and at least 5 mol % NGL, regardless of how or where the gas mixture is obtained.

A more detailed description of the present invention follows below. Each of the appended claims defines a separate invention, which for infringement purposes is recognized as including equivalents to the various elements or limitations specified in the claims. Depending on the context, all references to the "invention" may in some cases refer to certain specific embodiments only. In other cases, references to the "invention" refer to subject matter recited in one or more, but not necessarily all, of the claims. Each of the inventions is described in greater detail below, including specific embodiments, versions, and examples, but the inventions are not limited to these embodiments, versions, or examples. These are included to enable a person with ordinary skill in the art to make and use the inventions when the information in this disclosure is combined with publicly available information and technology.

The following detailed description illustrates embodiments of the present disclosure. These embodiments are described in enough detail to enable a person of ordinary skill in the art to practice these embodiments. It should be understood, however, that the embodiments and examples described here are given by way of illustration only, and not by way of limitation. The embodiments are chosen and described so that others skilled in the art may appreciate and understand the principles and practices of the present teachings. Various substitutions, modifications, additions, and rearrangements is made that remain potential applications of the disclosed processes. Therefore, the description that follows is not to be taken as limiting the scope of the appended claims. In particular, an element associated with a particular embodiment should not be limited to association with that particular embodiment but should be assumed to be capable of association with any embodiment discussed here.

Figure 5:
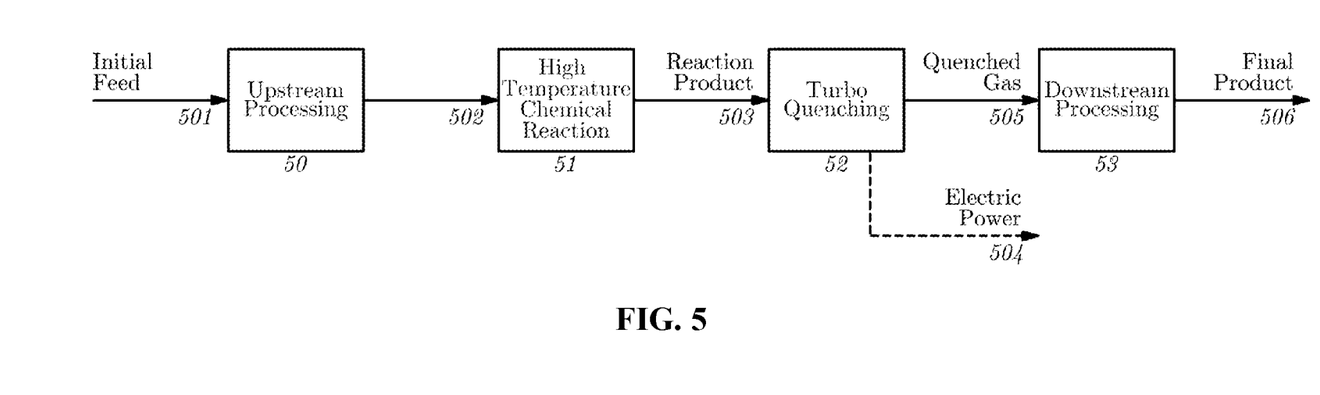
FIG. 5 depicts a block diagram illustrating a general chemical process in which turboquenching is used to lower the temperature of a matter stream after a high-temperature chemical reaction, according to one or more embodiments described herein.

FIG. 5 depicts a block diagram illustrating a general chemical process in which turboquenching is used to lower the temperature of a stream after a high-temperature chemical reaction, according to one or more embodiments provided herein. An initial feed or feed stream 501 can be preprocessed in one or more upstream processing units 50 to provide a first processed stream or resulting mixture 502. The resulting stream or mixture 502 can then be further processed or reacted using one or more other higher temperature reactors or conversion units 51 to provide a reaction product stream 503. The reaction product stream 503 can have a temperature above 200° C., or above 500° C., or above 700° C. and a pressure above 2 bars, or above 5 bars. The reaction product stream 503 can then be quenched in the absence of any quenching fluid in the turboquenching unit 52, using one or more turboquenchers.

The terms "turboexpander" and/or "turboquencher" are used interchangeably and refer to any suitable device across which pressure from the entering fluid can be decreased (i.e. expanded) and work can be extracted. Such expansion is generally isentropic. As work is extracted because of the fluid expansion, the exiting stream is reduced in enthalpy and hence in temperature. The extracted work can be converted to other forms of energy such as electricity (i.e. electrical power) 504.

Suitable turboexpanders can include rotatory machines with rotational blades. The blades can rotate at high rotational velocities, thereby providing low residence time for the gases passing through such machines. The rotational speed can be generally (but not necessarily) in the range of thousands of revolutions per time (rpm). Suitable turboexpanders can also include reciprocating expansion engines, as well as centrifugal or axial-flow turbine.

Figure 6:
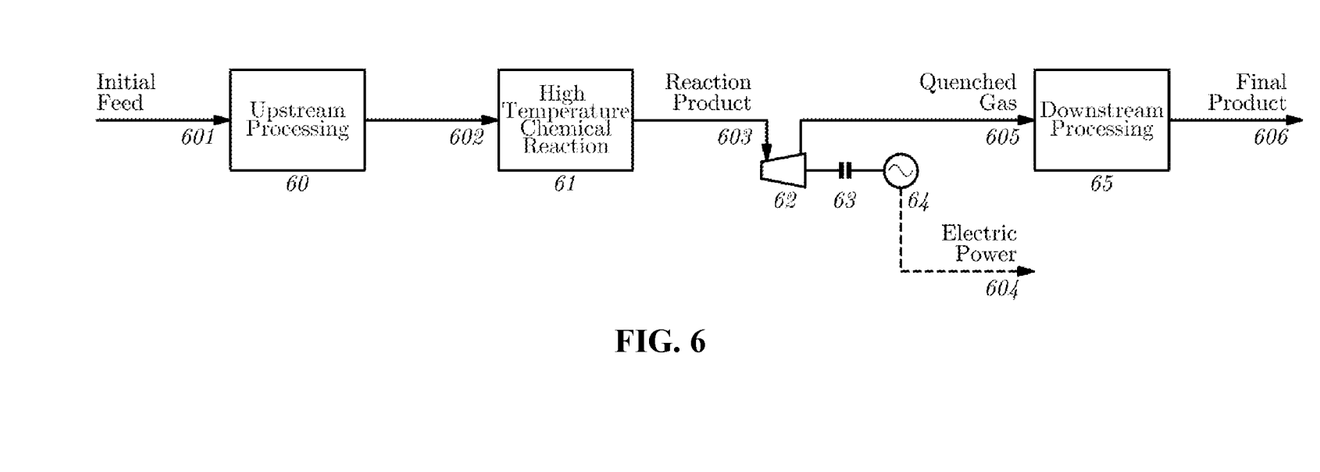
FIG. 6 shows additional detail of the turboquenching system, according to one or more embodiments described herein.

FIG. 6 shows additional details of the turboquenching section 52. As depicted, the turboquenching unit 52 can include three main elements: a turboexpander 62, an electric generator 64, and a coupling element 63. The turboexpander 62 takes advantage of the reaction product pressure (stream 503) being greater than the ambient pressure to lower its temperature while also generating mechanical power. The coupling element 63 can transfer mechanical energy produced in the turboexpander 62 to the electric generator 64, which can produce electric power 504. The net effect can be that the reaction product temperature can be significantly reduced in a short period of time. The quenched gas stream 505 can be then transported to one or more downstream processing units 65 to provide the final product 506. Although FIG. 6 shows a single turboexpander 62 and a single electric generator 64, in practice, the system might contain multiple expanders, multiple generators, and/or intermediate heaters to further maximize the power output, as desired.

Figure 7:
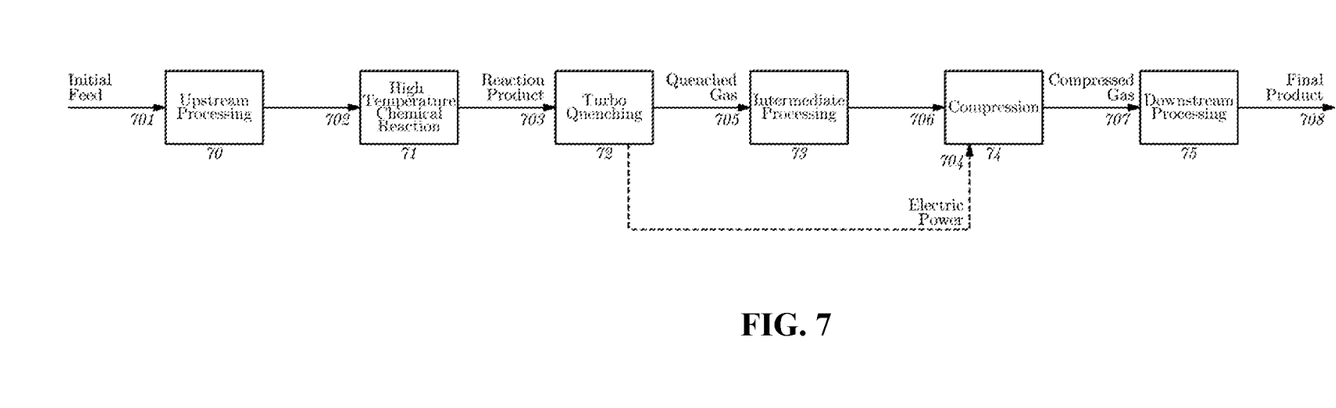
FIG. 7 depicts a block diagram illustrating a general chemical process in which turboquenching is used to lower the temperature of a matter stream after a high-temperature chemical reaction, and the electric power coproduced is used in the subsequent compression step, according to one or more embodiments described herein.
Figure 8:
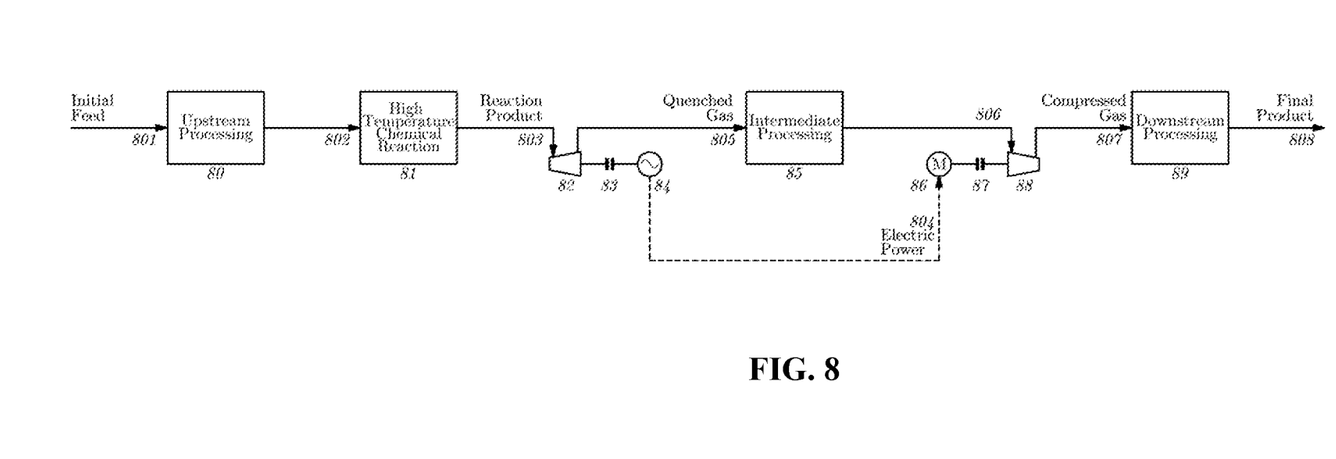
FIG. 8 shows additional detail of the coupling between turboquenching and compression, according to one or more embodiments described herein.

FIGS. 7 and 8 depict a situation where electric power 504 from turboquenching unit 72 can be used to run, at least in part, one or more compressors within compression unit 74 to provide a compressed gas stream 707. The compressed gas stream 707 can then be introduced to the downstream processing units 53, where it eventually leaves the system as the final product steam 506. Referring to FIGS. 7 and 8, the turboquenching unit can include three main components: a turboexpander 82, an electric generator 84, and a coupling element 83. The electric generator 84 can be electrically coupled with an electrical motor 86, which in turn can be mechanically coupled with the compressor 88 through a coupling element 87. Although FIG. 8 shows only one compression step, in practice the system might include multiple compressors, stages, and/or intercoolers.

Figure 9:
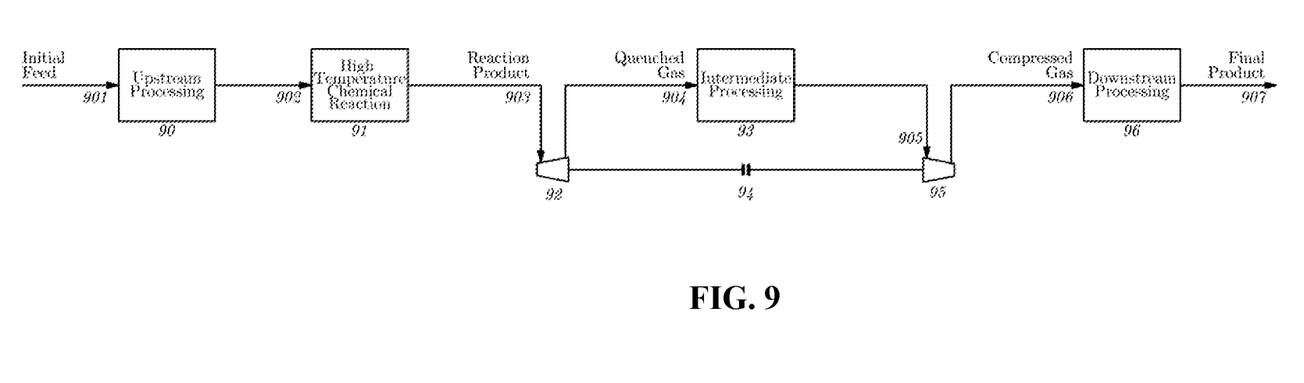
FIG. 9 illustrates the mechanical integration between turboquenching and compression, according to one or more embodiments described herein.

FIG. 9 illustrates a process in which the turboexpander 92 can be mechanically connected to a compressor 95 through a coupling element 94. This configuration uses less equipment than the one illustrated in FIG. 8 while maintaining the same benefit of using the expansion step to provide the necessary energy for compression. Although FIG. 9 shows only one compressor in practice the system might include multiple compressors, stages, and/or intercoolers.

Figure 10:
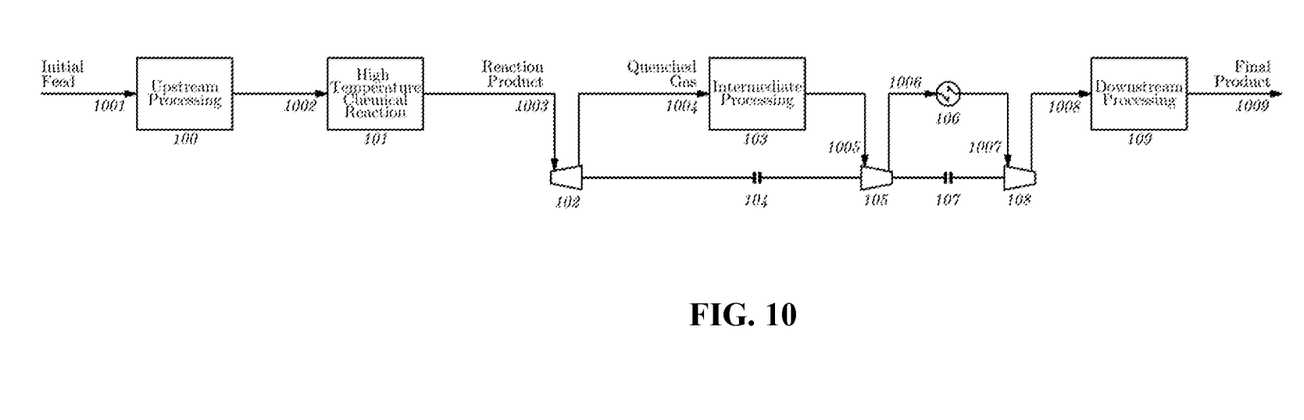
FIG. 10 illustrates the use of multiple compressors in the compression section and their integration with the turboquencher. This figure also shows the use of intercoolers between compressors, according to one or more embodiments described herein.

FIG. 10 illustrates a case in which the compression step can be performed using two compressors 1005, 1008, and at least one intercooler 1006. The compression step can be mechanically coupled with the turboexpander 1002, through a coupling element unit 1004. However, in this case, there can be a mechanical coupling element 1007 that links the two compressors 1005, 1008. This arrangement has the benefit of allowing higher outlet pressures after the compression step. It also reduces the energy consumption required for compression as it incorporates the at least one intercooler 1006 between stages.

In one or more particular embodiments, the initial feed stream 501 can be or can include a mixture of hydrocarbons, a raw shale gas stream or raw natural gas stream, or other raw hydrocarbon stream that can be obtained directly (i.e. without processing to remove water and/or acid gas) from a reservoir, wellhead, or pipeline. Suitable feed streams 501 can also originate from a refinery, such as from a FCC, coker, cracking reactor, and pyrolysis gasoline (pygas). Suitable gas mixtures can also be or can include coal gas.

Any of the forgoing configurations can be used to convert one or more paraffins (saturated hydrocarbons) within the initial feed stream 501 to one or more olefins (unsaturated hydrocarbons) which can be further converted to one or more oligomers. The initial feed stream 501 can be treated to remove acid gas and/or water within the upstream processing unit 50 to provide a "dry shale gas" or "sweet and dry shale gas" as stream 502. For simplicity and ease of description, the terms "shale gas" or "natural gas" or "dry shale gas" and "sweet and dry shale gas" all refer to any gas mixture containing at least 50 mol % methane and at least 5 mol % NGL.

The upgraded stream 502 can then be processed within the higher temperature processing unit 51. The higher temperature processing unit 51 can be one or more thermal or catalyst crackers, steam methane reformers, or other dehydrogenation units for converting one or more paraffins in the stream 502 to one or more olefins in gas stream 503. Suitable crackers are described in US patents U.S. Pat. No. 5,181, 990A and US20090252660A1. The higher temperature processing unit 51 can be a single processing unit or multiple processing units arranged in parallel or series. The higher temperature processing unit 51 can operate at any temperature between about 550° C. and 950° C., and at any pressure between about 1 bar and 30 bars. For example, the reaction product stream 503 exiting the higher temperature processing unit 51 can have a temperature above 200° C., or above 500° C., or above 700° C. and a pressure above 2 bars, or above 5 bars. The reaction product stream 503 can then be quenched in the absence of any quenching fluid in the turboquenching unit 52, using one or more turboexpanders.

The operating temperature and pressure can change to meet any design specifications.

The reaction product stream 503 exiting the higher temperature processing unit 51 can contain methane and one or more $C_{2+}$ hydrocarbons. Stream 503 can then be rapidly cooled or quenched in the turbo quenching unit 52, thereby producing electric power 504 and the quenched gas stream 505. The quenched gas 505 can then be introduced to one or more oligomerization reactors or systems within the downstream processing unit 53 where the olefins in stream 505 can be converted to one or more oligomers in the product stream 506. The oligomerization process can operate at a relatively lower temperature (200° C. to 600° C.) and medium pressure (1 bar to 50 bar). The oligomerization process can operate at a temperature lower than the inlet temperature. The typical operating pressure ranges from about 5 bar to about 30 bar and the operating temperature typically ranges from about 100° C. to about 300° C. The product stream 506 exiting the oligomerization process 53 can contain a mixture of C4-C26 hydrocarbons with a majority of the higher molecular weight hydrocarbons being greater than C6, and preferably C10-C18, or even more carbon atoms.

By "oligomer(s)", it is meant dimers, trimers, tetramers, and other molecular complexes having less than 26 repeating units. Additionally, olefin products with carbon numbers, which are not multiples of the starting reactant are also produced. Oligomers provided herein are typically gases or liquids at ambient temperature, and can include low melting solids, including waxes, at ambient temperature. In some embodiments, the oligomers provided herein, which are suitable for production of gasoline and diesel fuels, can have an atomic weight or molecular weight of less than 1000 AMU (Da), such as about 500 or less, 400 or less, 300 or less, or 200 or less. The molecular weight of the oligomer, for example, can range from a low of about 50, 250 or 350 to a high of about 500, or 1,000 AMU (Da).

EXAMPLES

The foregoing discussion can be further described with reference to the following non-limiting examples. The process simulations were implemented using Aspen Plus and Chemkin.

Example 1 (Comparative Example)

The results of a cracking process of a matter stream using a cracking reactor are presented. The goal of this example can be to provide a description of the prior art cracking process as it can be one of the most important applications in which quenching can be used. The reactor implemented can be analogous to the steam cracker shown in FIG. 4B, unit 41, with the difference being that, instead of steam, methane can be used as a diluent. The benefits of replacing steam with methane are presented in the allowed US patent application US2020/0308086A1 and US2020/0308088A1.

Figure 11:
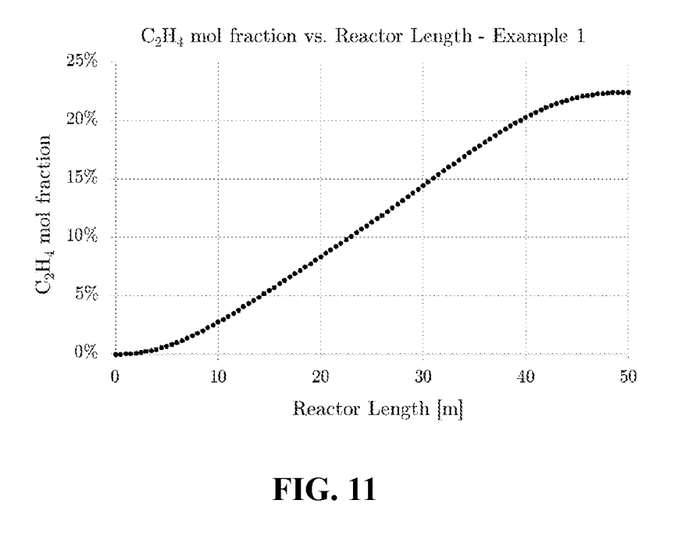
FIG. 11 shows the ethylene composition profile across the length of the reactor for example 1, according to one or more embodiments described herein.

The conditions of the inlet gas are presented in Table 1. This stream can be imagined as the result of mixing steams 402 and 403 and preheating the resulting mixture to 620° C. The mixture enters the radiant section of the cracker which can include a long tubular reactor through which the inlet gas flows while receiving energy from the combustion of the fuel gas 404. As a result, the inlet gas undergoes a series of chemical processes, generating mainly ethylene and hydrogen. There can be no single set of conditions under which steam cracking reaction takes place. This leads to the need to optimize the operating conditions in order to maximize the ethylene yield while minimizing the operating cost. Table 3 present the dimensions of the reactor used in this example. The value of the heat flow reported corresponds to the optimum value found for this case. The information on the gas coming out of the reactor can be shown in table 2. FIG. 11 shows the ethylene composition profile across the length of the reactor.

From FIG. 11, the ethylene composition, initially 0%, continuously increases until reaching its maximum, of ~23%, at the end of the reactor. The ethylene profile does not start growing immediately after the gas enters the reactor since the gas requires some time, in this case, expressed as a length, to reach the temperature at which the reaction becomes significant. After the ~7m mark, the composition increase can be steady. This behavior remains constant until the ~43m mark, in which the slope starts to decrease, becoming almost flat at the 50m mark. This can be due to the depletion of the reactants and the termination of the main reaction in which the reactants mainly produce ethylene.

Figure 12:
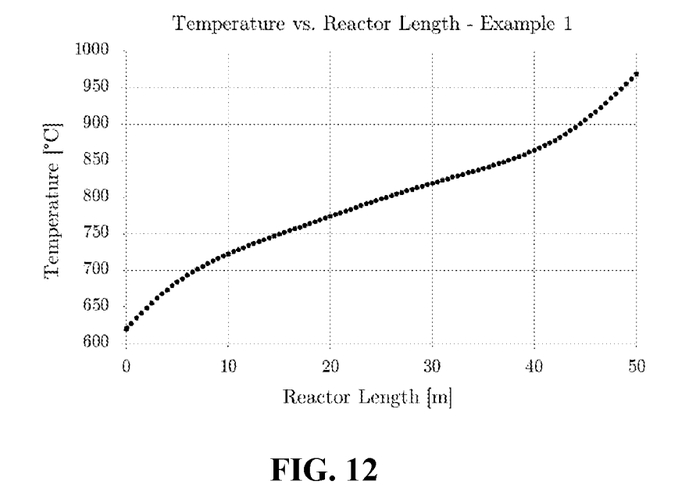
FIG. 12 shows the temperature profile across the length of the reactor for example 1, according to one or more embodiments described herein.

FIG. 12 shows the temperature profile across the length of the reactor in FIG. 11. The first ~10m of the reactor are mainly used to increase the gas temperature and reach the reaction condition. Subsequently, the temperature increase can be decelerated as more energy can be used for the chemical reaction instead of being used to increase the temperature. In this context, the chemical reaction acts as a buffer against the increase in temperature. After the ~40m mark, we can see how the slope of the temperature increases again. This can be due to the depletion of the reactants and marks the end of the buffer action of the chemical reaction. Without any further energy sink, the temperature can be free to increase at a higher rate again.

TABLE 1

Key information on the inlet gas entering the reaction section of the steam cracker in Example 1.

|  | Units | Value |
|---|---|---|
| Temperature | ° C. | 620 |
| Pressure | bar | 6 |
| Mass Flow | kg/s | 0.5 |
| $CH_4$ | mol fraction | 0.65 |
| $C_2H_6$ | mol fraction | 0.2 |

TABLE 1-continued

Key information on the inlet gas entering the reaction
section of the steam cracker in Example 1.

|  | Units | Value |
|---|---|---|
| $C_3H_8$ | mol fraction | 0.1 |
| $C_4H_{10}$ | mol fraction | 0.05 |
| $H_2O$ | mol fraction | 0.0 |

TABLE 2

Key information on the gas after reaction
in the steam cracker from Example 1.

|  | Units | Value |
|---|---|---|
| Temperature | °C. | 942.3 |
| Pressure | bar | 4.6 |
| Mass Flow | kg/s | 0.5 |
| $CH_4$ | mol fraction | 0.610 |
| $C_2H_6$ | mol fraction | 0.006 |
| $C_2H_4$ | mol fraction | 0.224 |
| $H_2$ | mol fraction | 0.140 |
| $C_3H_8$ | mol fraction | 0.000 |
| $C_3H_6$ | mol fraction | 0.004 |
| $C_{4+}$ | mol fraction | 0.011 |
| Other | mol fraction | 0.005 |
| $H_2O$ | mol fraction | 0.000 |

TABLE 3

Key information for the steam cracking unit used in Example 1.

|  | Units | Value |
|---|---|---|
| Reactor Length | m | 50 |
| Reactor Diameter | in | 4 |
| Heat Flow to Reactor | W/m | 31100 |

Example 2

As a second example, two scenarios are compared: first, the scenario in which the reaction product stream remains at the outlet temperature after completing its reaction, and second, the scenario in which the reaction product stream can be instantly quenched to 600° C. The goal of this example can be to show the need to quench the product stream after the reaction.

Figure 13:
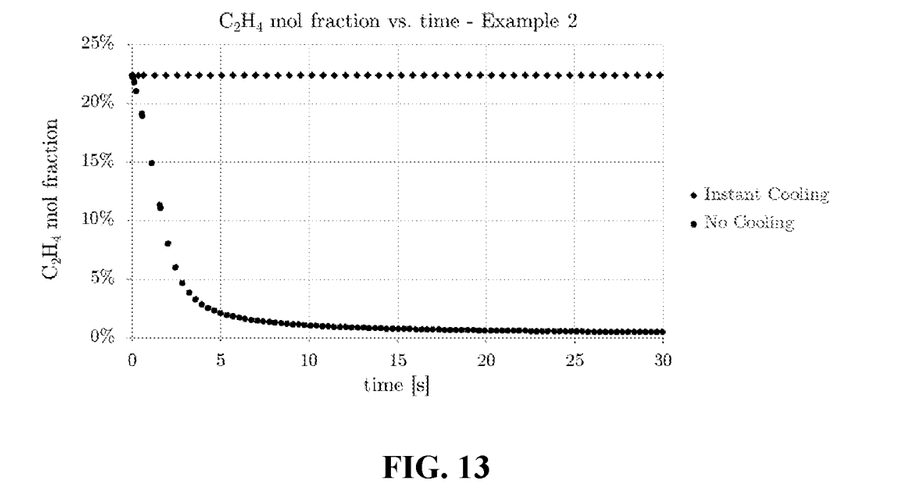
FIG. 13 shows the ethylene composition profiles across the length of the reactor for example 2, according to one or more embodiments described herein.

Example 2 uses the outlet product from Example 1. The results obtained are summarized in FIG. 13. Here, it can be possible to see how, in the case where there can be no cooling of the product stream, the ethylene mol fraction reduces from its maximum at ~23% to ~0.5% in 30 seconds. This result contrasts with the instant cooling scenario in which the ethylene composition can remain completely constant. In practice, it can be impossible to achieve instantaneous cooling. So, every real scenario will take place between these two limit cases. The faster the cooling is, the closer the outlet ethylene composition will be to the instant cooling scenario. Similarly, the longer the cooling takes, the closer the outlet ethylene composition will be to the no cooling scenario.

Example 3

As a third example, the results of expanding the dehydrogenation product to rapidly reduce its temperature are presented. The goal of this example can be to show the possibility of quenching without using any quenching fluid while also coproducing electric power.

Example 3 uses the outlet composition from Example 1. This stream can be fed into a turboexpander in which it can be rapidly expanded to a pressure of 1.4 bars. This process rapidly reduces the gas temperature while also producing electric power. The situation can be analogous to the one illustrated in FIG. 6. The results are summarized in Table 4 and presented in graphical form in FIGS. 14 and 15. All cases consider a turbine efficiency of 80%.

Figure 14:
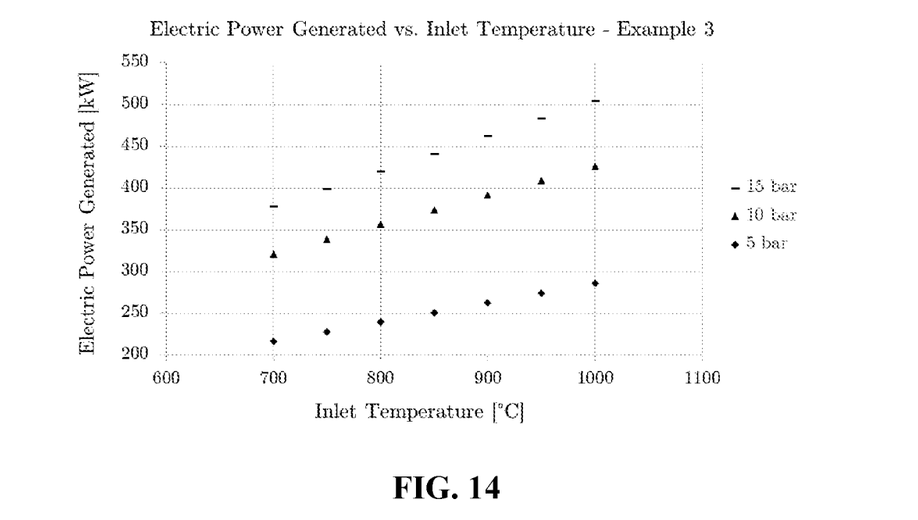
FIG. 14 shows the electric power generated during turboquenching vs. the inlet gas temperature for different inlet gas pressures, according to one or more embodiments described herein.

FIG. 14 shows the correlation between the electric power generated and the inlet gas temperature for different inlet gas pressures. The outlet gas pressure can be 1.4 bars for all cases. The results show that power generation can be favored at high inlet pressures and high inlet temperatures.

Figure 15:
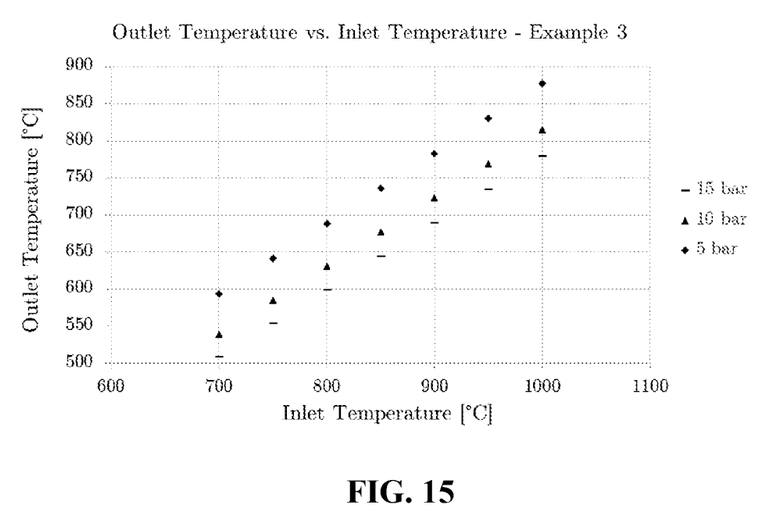
FIG. 15 shows the outlet temperature of the quenched gas vs. the inlet gas temperature for different inlet gas pressures, according to one or more embodiments described herein.

FIG. 15 shows the correlation between the outlet gas temperature and the inlet gas temperature for different inlet gas pressures. The outlet gas pressure can be 1.4 bars for all cases. The results show that the higher the inlet gas pressure, the lower the outlet gas temperature can be for the same inlet gas temperature. Consequently, more rapid quenching can be achieved as well.

TABLE 4

Key information about the impact of the turboexpander
Inlet Temperature and Inlet Pressure over the Electric
Power Generated and the Outlet Temperature.

| Inlet Temperature [° C.] | Inlet Pressure [bar] | Mass Flow [kg/s] | Electric Power Generated [kW] | Outlet Temperature [° C.] | Outlet Pressure [bar] |
|---|---|---|---|---|---|
| 700 | 5 | 0.5 | 217 | 594 | 1.4 |
| 700 | 10 | 0.5 | 322 | 540 | 1.4 |
| 700 | 15 | 0.5 | 379 | 509 | 1.4 |
| 750 | 5 | 0.5 | 228 | 641 | 1.4 |
| 750 | 10 | 0.5 | 339 | 586 | 1.4 |
| 750 | 15 | 0.5 | 400 | 554 | 1.4 |
| 800 | 5 | 0.5 | 240 | 688 | 1.4 |
| 800 | 10 | 0.5 | 357 | 632 | 1.4 |
| 800 | 15 | 0.5 | 421 | 600 | 1.4 |
| 850 | 5 | 0.5 | 251 | 736 | 1.4 |
| 850 | 10 | 0.5 | 374 | 678 | 1.4 |
| 850 | 15 | 0.5 | 442 | 645 | 1.4 |
| 900 | 5 | 0.5 | 263 | 783 | 1.4 |
| 900 | 10 | 0.5 | 392 | 724 | 1.4 |
| 900 | 15 | 0.5 | 463 | 690 | 1.4 |
| 950 | 5 | 0.5 | 274 | 830 | 1.4 |
| 950 | 10 | 0.5 | 409 | 769 | 1.4 |
| 950 | 15 | 0.5 | 484 | 735 | 1.4 |
| 1000 | 5 | 0.5 | 286 | 878 | 1.4 |
| 1000 | 10 | 0.5 | 427 | 815 | 1.4 |
| 1000 | 15 | 0.5 | 504 | 780 | 1.4 |

The highest generated electric power reported in Table 4 corresponds to 504 kW obtained at an inlet temperature and inlet pressure of 1000° C. and 15 bars, respectively. On the other hand, the minimum electric power generated corresponds to 217 kW at an inlet temperature and inlet pressure of 700° C. and 5 bars, respectively. From here, it can be possible to see that the generated power varies among a wide range of values and that it can be tailored to a particular value with proper choices in operating conditions. The subsequent adiabatic compression process of the same stream for downstream processing from 1.4 bars and ambient temperature to 30 bars would consume ~369 kW in a compressor efficiency of 80%. By balancing the outlet power from the turboexpander with the one needed for compression, it can be possible to completely provide all the energy required for compression through the turboquenching process. At the same time, the inlet gas would also be quenched. This situation would be analogous to those presented in FIGS. 7 to 10.

Certain embodiments and features have been described using a set of numerical upper limits and a set of numerical lower limits. Ranges, including the combination of any two values, e.g., the combination of any lower value with any upper value, the combination of any two lower values, and/or the combination of any two upper values, are contemplated unless otherwise indicated. Certain lower limits, upper limits, and ranges appear in one or more claims below. All numerical values are "about" or "approximately" the indicated value, meaning the values take into account experimental error, machine tolerances, and other variations that would be expected by a person with ordinary skill in the art.

The explanation above has also outlined features of several embodiments so that those skilled in the art can better understand the present disclosure. They should realize that they can readily use the present disclosure as a basis for designing or modifying other methods or devices for carrying out the same purposes and/or achieving the same advantages of the embodiments disclosed here. Those skilled in the art should also realize that such equivalent constructions do not depart from the spirit and scope of the present disclosure. Therefore, they can make various changes, substitutions, and alterations here without departing from the spirit and scope of the present disclosure, and the scope thereof is determined by the claims that follow.

Various terms have been defined above. To the extent that a term used in a claim is not defined above, it should be given the broadest definition that those in the pertinent art have given that term as reflected in at least one printed publication or issued patent. Furthermore, all patents, test procedures, and other documents cited in this application are fully incorporated to the extent that such disclosure is not inconsistent with this application and covers all jurisdictions in which such incorporation is permitted.

What is claimed is:

1. A process for quenching a high-temperature and above atmospheric pressure stream to a lower temperature without the need of a quenching fluid, comprising:
    providing an outlet stream from a high temperature conversion reaction selected from the group consisting of steam cracking, catalytic cracking, and pyrolysis, wherein the outlet stream has a temperature of 500° C. or above and a pressure above atmospheric pressure;
    directly expanding the outlet stream in a turboexpander to generate work and provide a quenched stream, wherein the quenching occurs without any intermediate heat exchange step; and
    recovering the work generated by the turboexpander to produce electric power.

2. The process of claim 1, wherein a feed stream to the high temperature conversion reaction comprises a mixture of hydrocarbons selected from the group consisting of ethane, propane, butane, and natural gas liquids (NGLs).

3. The process of claim 1, wherein the high temperature conversion reaction is steam cracking for producing ethylene.

4. The process of claim 3, wherein the feed stream to the high temperature conversion reaction comprises methane.

5. The process of claim 3, wherein the feed stream to the high temperature conversion reaction comprises shale gas.

6. The process of claim 1, wherein the high temperature conversion reaction produces a mixture of carbon monoxide and hydrogen.

7. The process of claim 1, wherein the temperature of the outlet stream from the high temperature conversion reaction is above 750° C. and wherein the pressure of the outlet stream from the high temperature conversion reaction is above 2 bars.

8. The process of claim 1, further comprising oligomerizing one or more olefins within the quenched stream.

9. The process of claim 1, wherein the electric power is used to operate a motor coupled to a compressor.

10. The process of claim 1, wherein the turboexpander is mechanically coupled to an electric generator to convert mechanical energy into electrical energy.

11. The process of claim 1, wherein the high temperature conversion reaction is steam cracking.

12. A process for quenching a high-temperature and above atmospheric pressure stream to a lower temperature without the need of a quenching fluid, comprising:
    providing an outlet stream from a high temperature conversion reaction selected from the group consisting of steam cracking, catalytic cracking, and pyrolysis, wherein the outlet stream has a temperature of 500° C. or above and a pressure above atmospheric pressure;
    directly expanding the outlet stream in a turboexpander to generate work and provide a quenched stream, wherein the quenching occurs without any intermediate heat exchange step;
    recovering the work generated by the turboexpander to provide electrical power; and
    powering a compressor to compress the quenched stream using the provided electrical power.

13. The process of claim 12, wherein a feed stream to the high temperature conversion reaction comprises a mixture of natural gas liquids.

14. The process of claim 12, wherein the high temperature conversion reaction is steam cracking for producing ethylene.

15. The process of claim 14, wherein the feed stream to the high temperature conversion reaction comprises methane, shale gas, or mixtures thereof.

16. The process of claim 12, wherein the high temperature conversion reaction produces a mixture of carbon monoxide and hydrogen.

17. The process of claim 12, wherein the temperature of the outlet stream from the high temperature conversion reaction is above 750° C. and the pressure of the outlet stream from the high temperature conversion reaction is above 2 bars.

18. The process of claim 12, wherein the outlet stream is expanded within a turboexpander that is directly coupled to one or more compressors.

19. A process for upgrading natural gas liquids (NGL), comprising:
    providing a natural gas comprising methane and one or more $C_{2+}$ hydrocarbons;
    dehydrogenating at least a portion of the one or more $C_{2+}$ hydrocarbons to provide an outlet stream comprising one or more $C_{2+}$ olefinic hydrocarbons at a temperature of 550° C. to 950° C. and a pressure above atmospheric pressure;
    directly expanding the outlet stream in a turboexpander to generate work and provide a quenched stream comprising the one or more $C_{2+}$ olefinic hydrocarbons at a temperature lower than the inlet temperature, wherein the expansion occurs without any intermediate heat exchange;

recovering the work generated by the turboexpander by coupling the turboexpander with an electric generator to provide electrical power;

compressing the quenched stream using a compressor driven by the provided electrical power; and oligomerizing the compressed stream to provide a product stream comprising one or more C4 to C26 oligomers.

20. The process of claim 19, wherein the outlet stream comprising the one or more $C_{2+}$ olefinic hydrocarbons is quenched without the use of a quenching fluid and the outlet stream is provided from any one or more thermal crackers, catalyst crackers, steam methane reformers, or other dehydrogenation units.

* * * * *